United States Patent

Rao

(10) Patent No.: US 9,364,659 B1
(45) Date of Patent: Jun. 14, 2016

(54) SMART LEAD FOR DEEP BRAIN STIMULATION

(71) Applicant: Dantam K. Rao, Schenectady, NY (US)

(72) Inventor: Dantam K. Rao, Schenectady, NY (US)

(*) Notice: Subject to any disclaimer, the term of this patent is extended or adjusted under 35 U.S.C. 154(b) by 0 days.

(21) Appl. No.: 14/697,425

(22) Filed: Apr. 27, 2015

(51) Int. Cl.
*A61B 5/04* (2006.01)
*A61N 1/05* (2006.01)
*A61B 5/0478* (2006.01)

(52) U.S. Cl.
CPC .......... *A61N 1/0534* (2013.01); *A61B 5/04001* (2013.01); *A61B 5/0478* (2013.01); *A61N 1/0529* (2013.01); *A61N 1/0531* (2013.01)

(58) Field of Classification Search
CPC ............. A61B 5/04001; A61N 1/0534; A61N 1/0529; A61N 1/0531; A61N 5/0478
USPC .................................................. 600/377, 378
See application file for complete search history.

(56) References Cited

U.S. PATENT DOCUMENTS

| | | | |
|---|---|---|---|
| 3,804,098 A | 4/1974 | Friedman | |
| 5,003,992 A | 4/1991 | Holleman et al. | |
| 5,179,962 A | 1/1993 | Dutcher et al. | |
| 5,344,439 A | 9/1994 | Otten | |
| 5,458,629 A | 10/1995 | Baudino et al. | |
| 6,216,045 B1 | 4/2001 | Black et al. | |
| 6,265,691 B1 | 7/2001 | Cardineau et al. | |
| 6,326,587 B1 | 12/2001 | Cardineau et al. | |
| 6,569,160 B1 * | 5/2003 | Goldin ................... | A61B 18/12 600/427 |
| 6,606,521 B2 | 8/2003 | Paspa et al. | |
| 6,909,918 B2 | 6/2005 | Stypulkowski | |
| 6,988,006 B2 | 1/2006 | King et al. | |
| 7,047,084 B2 | 5/2006 | Erickson et al. | |
| 7,616,998 B2 | 11/2009 | Nuttin et al. | |
| 7,844,344 B2 | 11/2010 | Wahlstrand et al. | |
| 7,941,202 B2 | 5/2011 | Hetke et al. | |
| 7,941,213 B2 | 5/2011 | Markowitz et al. | |
| 8,442,653 B2 | 5/2013 | Gill | |
| 8,543,222 B1 | 9/2013 | Sochor | |
| 8,565,868 B2 | 10/2013 | Lee et al. | |
| 8,565,894 B2 | 10/2013 | Vetter et al. | |
| 8,739,403 B2 | 6/2014 | Hegland et al. | |
| 8,792,993 B2 | 7/2014 | Pianca et al. | |
| 8,805,541 B2 | 8/2014 | Wahlstrand et al. | |
| 8,862,242 B2 | 10/2014 | Pianca | |
| 2005/0159799 A1 | 7/2005 | Daglow et al. | |

(Continued)

OTHER PUBLICATIONS

M. Hariz, "Deep Brain Stimulation: New Techniques", Parkinsonism and Related Disorders, 2014, p. 192-196.

(Continued)

*Primary Examiner* — Matthew F Desanto

(57) ABSTRACT

Disclosed is a smart lead comprising a large number of micro-electrodes and macro-electrodes. The macro-electrodes are perforated, and contain several through-holes which are used to electrically join them with associated electrode-wires. The radial gaps that separate the macro-electrodes are filled with macro-electrode strips that carry a three-dimensional array of micro-electrodes. The nest of macro-electrodes with electrode-wires and micro-electrode strips are injection molded to form the smart lead. The signals sensed by micro-electrodes are used to locate the target neurons right at the first insertion of the smart lead, thereby greatly reducing the surgical time. A closed loop control software in automates location of the target neuron sites and limit the currents to stimulate only the target neurons, thereby reducing side-effects and increasing battery life.

2 Claims, 9 Drawing Sheets

(56) References Cited

U.S. PATENT DOCUMENTS

| | | | |
|---|---|---|---|
| 2007/0123765 A1* | 5/2007 | Hetke | A61B 5/04001 600/378 |
| 2008/0215125 A1 | 9/2008 | Farah et al. | |
| 2008/0269854 A1* | 10/2008 | Hegland | A61N 1/0534 607/116 |
| 2009/0054947 A1 | 2/2009 | Bourn et al. | |
| 2009/0187196 A1* | 7/2009 | Vetter | A61N 1/0534 606/129 |
| 2010/0030298 A1 | 2/2010 | Martens et al. | |
| 2010/0036468 A1 | 2/2010 | Decre et al. | |
| 2010/0082076 A1 | 4/2010 | Lee et al. | |
| 2010/0268298 A1* | 10/2010 | Moffitt | A61N 1/0534 607/45 |
| 2011/0047795 A1 | 3/2011 | Turner et al. | |
| 2012/0109262 A1 | 5/2012 | Martens | |
| 2012/0165911 A1 | 6/2012 | Pianca | |
| 2012/0184837 A1* | 7/2012 | Martens | A61B 5/0478 600/378 |
| 2013/0123600 A1* | 5/2013 | Tcheng | A61B 5/0478 600/378 |
| 2014/0130349 A1 | 5/2014 | Swanson et al. | |
| 2014/0163656 A1 | 6/2014 | Govea | |
| 2014/0288615 A1 | 9/2014 | Decre et al. | |
| 2015/0202432 A1* | 7/2015 | Somogyi | A61N 1/0534 607/116 |

OTHER PUBLICATIONS

S. Stanslaski et al., Design and Validation of a Fully Implantable, Chronic, Closed Loop Neuromodulation Device with Concurrent Sensing and Stimulation, IEEE Trans. Neural Systems and Rehabilitation Engineering, vol. 20, No. 4, pp. 410-421, Jul. 2012.

Medtronic, Activa PC+S Deep Brain Stimulation System enables research towards personalized treatment of neurological and psychological Diseases, Public Release, Dec. 5, 2013.

* cited by examiner

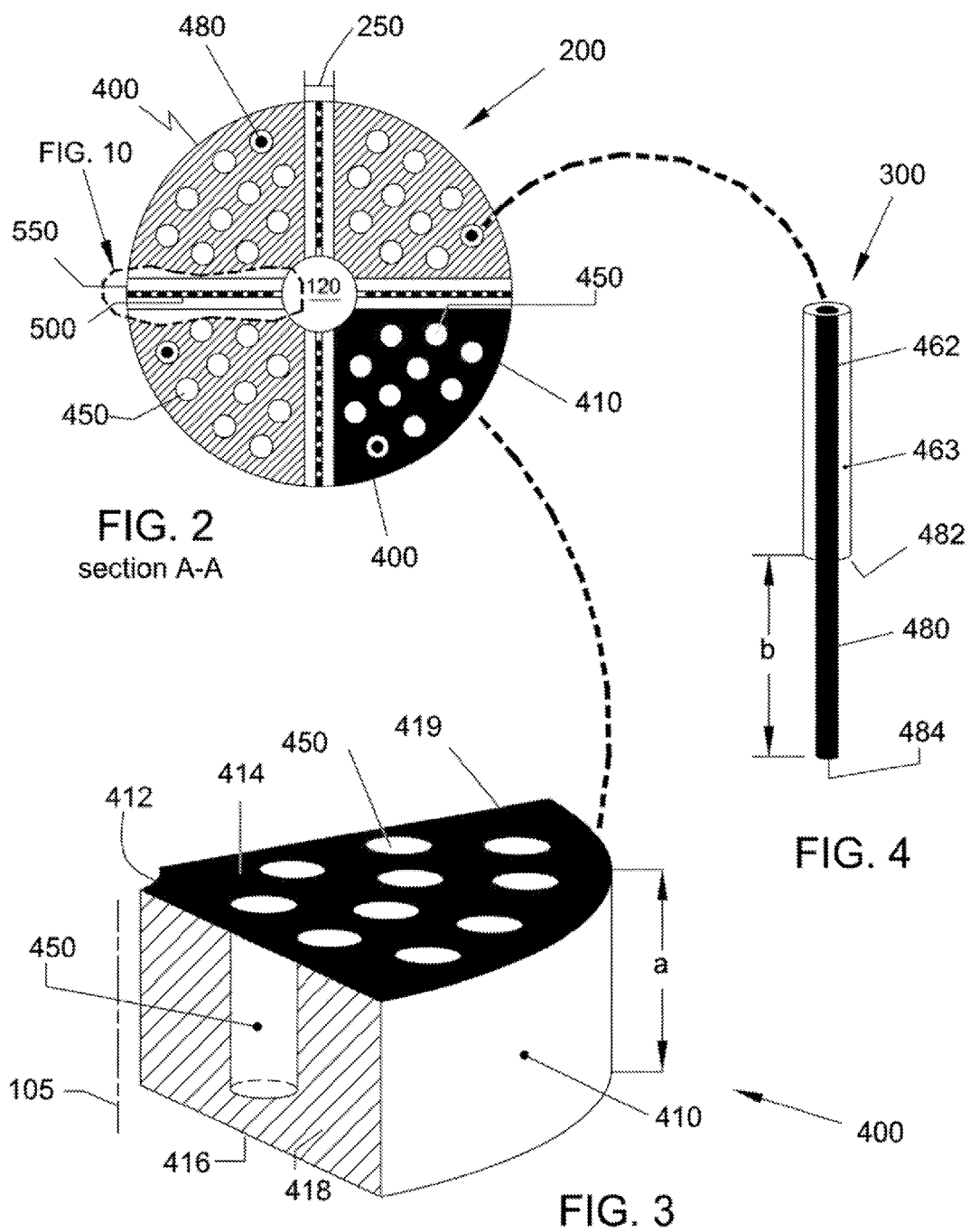

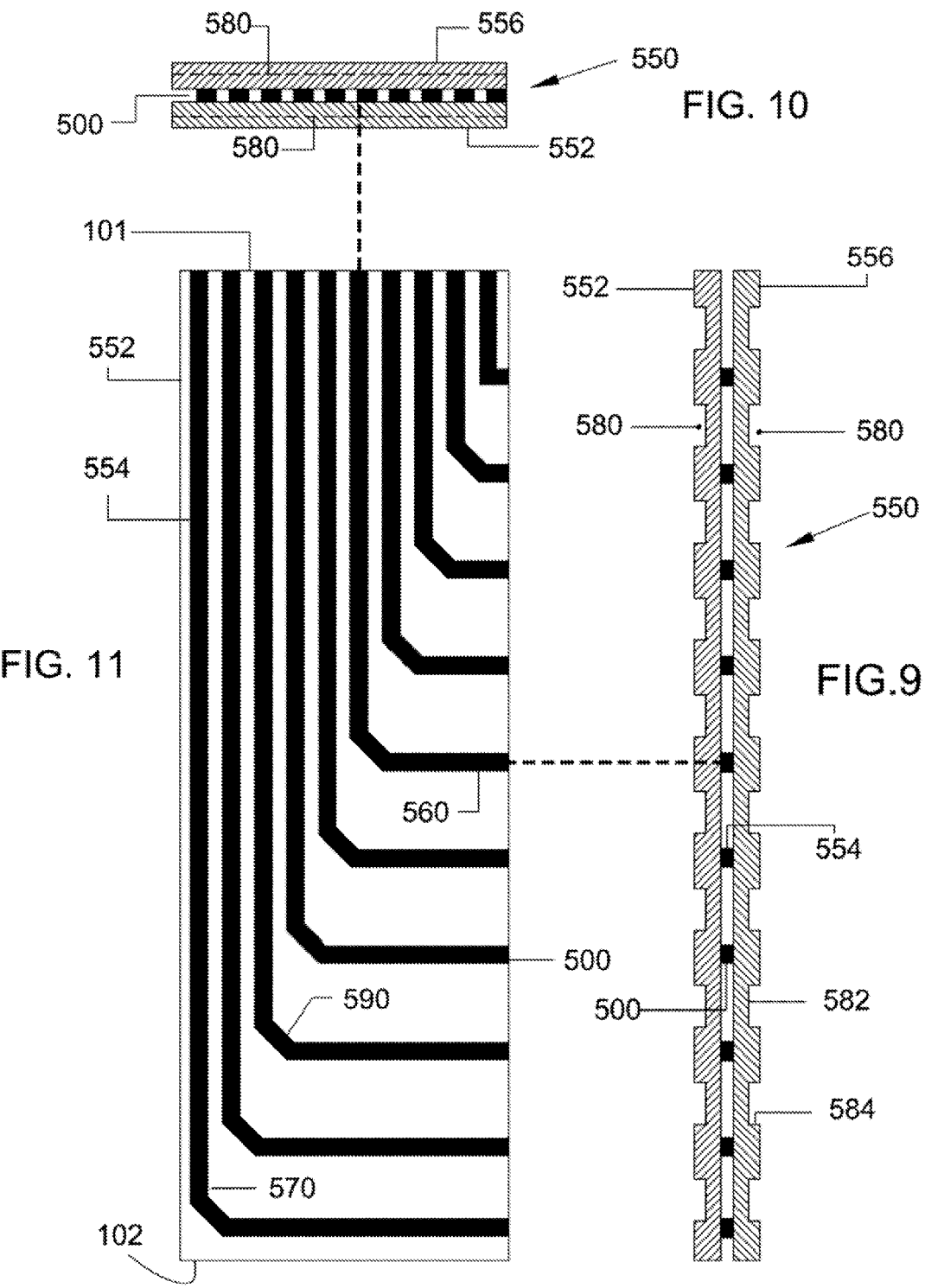

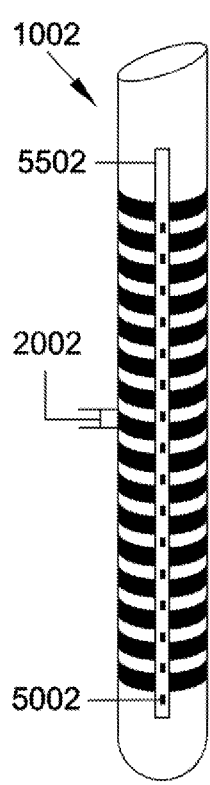 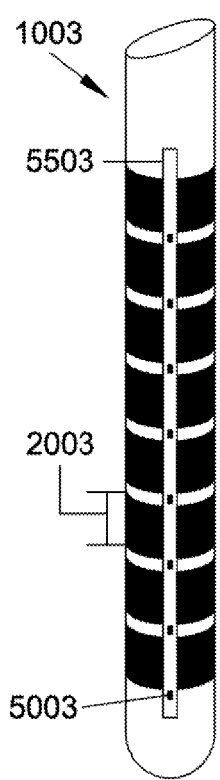 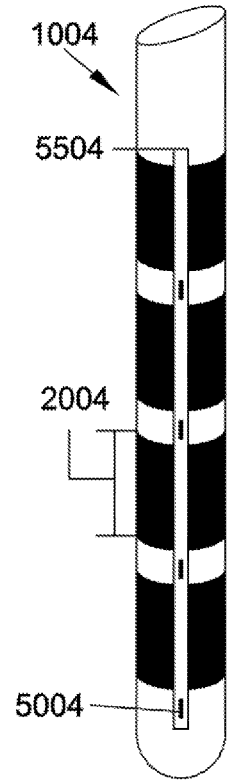 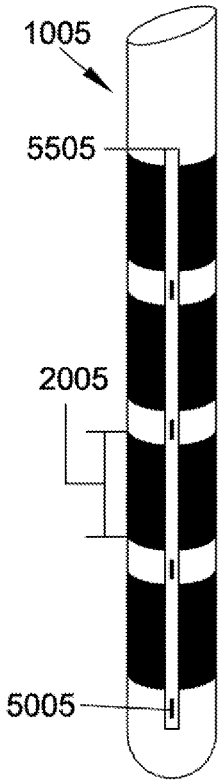
FIG. 13  FIG. 14  FIG. 15  FIG. 16
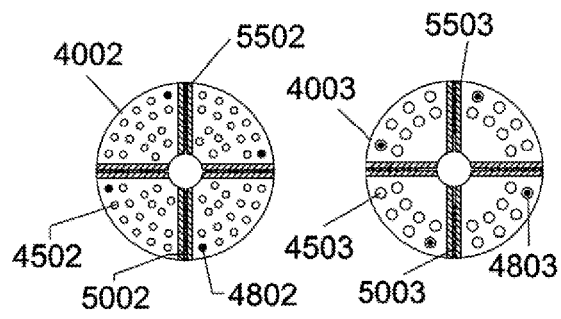 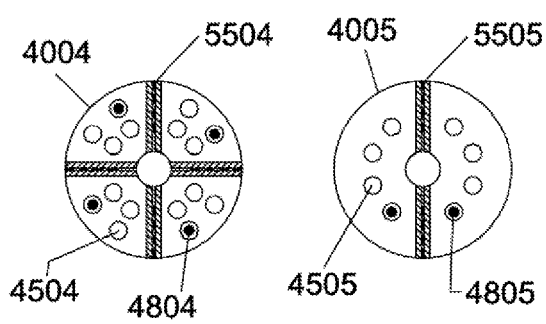
FIG. 13A  FIG. 14A  FIG. 15A  FIG. 16A

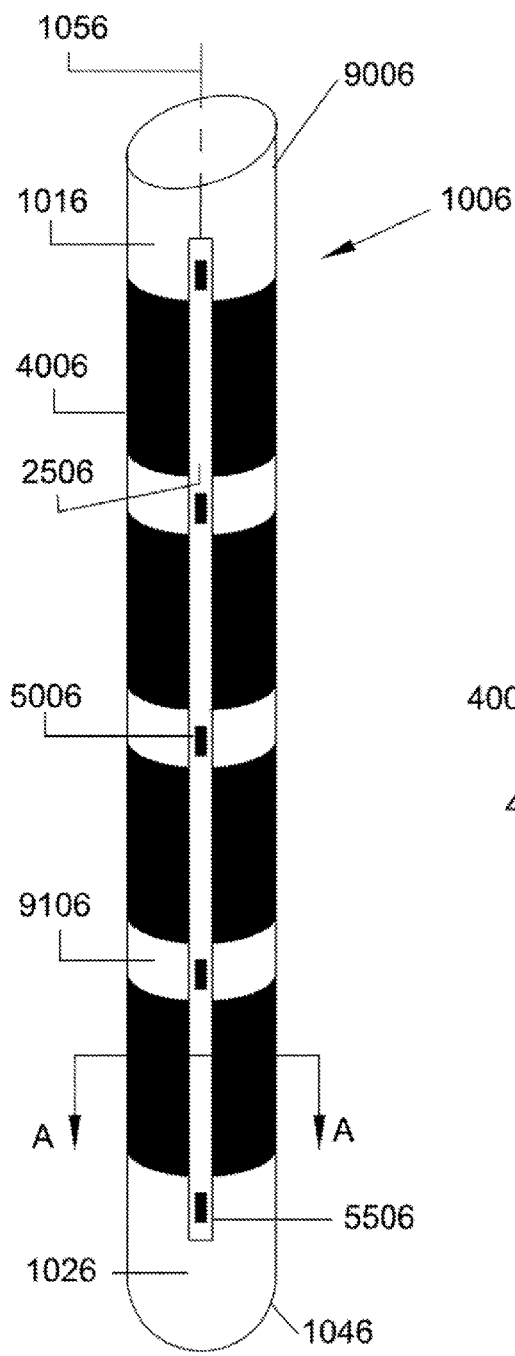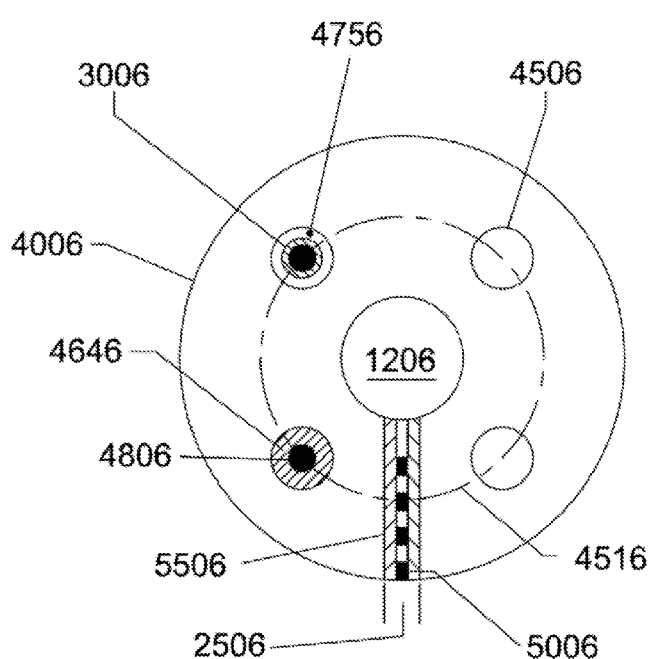
FIG. 17
FIG. 18
section A-A

SMART LEAD FOR DEEP BRAIN STIMULATION

TECHNICAL FIELD

The present disclosure relates to closed loop neuro-stimulation technologies, particularly to leads that contain both stimulating macro-electrodes and sensing micro-electrodes.

BACKGROUND

Deep Brain Stimulation (DBS) has been used to treat ailments such as Parkinson's disease, depression, epilepsy, paralysis, obsessive-compulsive disorder, essential tremor, dystonia, chronic pain, sleep disorder etc. In DBS, a neurosurgeon uses an implantable lead deep into the brain and inject currents into target neuron sites via its electrodes. These sites include Subthalamic Nucleus (STN), the Globus Pallidus Internal (GPi) etc. The target sites are very small (e.g., STN is ~4 mm diameter, 9 mm long ovoid). Accurately locating the target site and implanting a lead close to its center are critical to stimulate only the targeted neurons.

To locate the target site, currently a neurosurgeon inserts a recording micro-electrode that senses electrical signals produced by neurons. If the sensed signal is not identical to a desirable pattern, he retracts it and inserts another recording micro-electrode along a different trajectory. He repeats the process several times until he identifies a target site that will offer the best possible results. But the multiple passes of inserting/retracting recording electrodes in and out of the brain several times can rupture the fine blood vessels in the brain. Further, these multiple passes can take several hours. Reduction of this surgical time will obviously require micro-electrodes embedded within a DBS lead.

Implanting a lead exactly at the center of a target site right at the first time is currently nearly impossible as MRI, stereotactic equipment and brain shifts limit the accuracy. But currents from such off-centered lead can unintentional stimulation of neurons outside the target site, causing serious side effects such as suicidal tendency, double vision, worsened speech, dizziness etc. Reduction of such side effects will obviously require a large number of macro-electrodes, so a select group of macro-electrodes can be steered or focused only on the target neurons.

Prior art leads and systems are open loop, meaning that they do not contain recording micro-electrodes that are necessary for closed loop control. Examples of such prior art open loop leads include, a 4-electrode lead (model 3389) by Medtronic Inc., MN as described in U.S. Pat. No. 8,805,541, an 8-electrode lead by Boston Scientific, MA as described in U.S. Pat. No. 8,792,993, a 12-electrode lead by Aleva Neurotherapeutics SA, Switzerland as described in M. Hariz, "Deep Brain Stimulation: New Techniques", in *Parkinsonism and Related Disorders*, 2014, p. 192-196. This publication also describes a 32-electrode lead by Sapiens Steering Brain Stimulation, Netherlands. The Sapiens lead employs pad type electrodes that can entangle in the brain if they fail. This lead also does not contain micro-electrodes. A recent closed loop system by Medtronic Inc., MN, termed Activa® PC+S, uses two leads with four macro-electrodes at two different target sites. This system also does not contain micro-electrodes. Such prior-art open loop leads require substantially long surgical time; they are also prone to serious side affects as it is difficult to implant the lead close to the center of the target site right at the first instance.

SUMMARY OF THE INVENTION

The disclosed lead, termed "smart lead", is essentially a closed loop lead that embeds a large number of micro-electrodes (for sensing signals from neurons) along with a large number of macro-electrodes (for injecting current into neurons). The terms segment-electrode, perforated-electrode, macro-electrode are used interchangeably herein. A neurosurgeon implants the smart lead into the brain only once, along a trajectory determined initially by MRI. The micro-electrodes and macro-electrodes are electrically connected to an implanted medical device (IMD). A closed loop feedback controller in IMD will then use the signals sensed by the micro-electrodes to locate target neurons and steer currents by select macro-electrodes. Such smart lead can greatly reduce the surgical time, minimize the side effects and increase battery life.

The smart lead packs a large number of macro-electrodes and micro-electrodes into several electrode-rings that are equi-spaced between a distal end and a proximal end along a longitudinal axis. Each macro-electrode is an annular disc segment made of a conductive material. The segment spans an integral fraction of 360°, such as 60°, 90°, 180° etc. A preferable electrode-ring comprises four macro-electrodes in 90° segments separated by four radial gaps. Four elongated micro-electrode strips containing a three-dimensional array of micro-electrodes fill these four radial gaps. These micro-electrode strips engage and tightly lock all micro-electrodes in position. For example, a smart lead with 40 macro-electrodes and 40 micro-electrodes employs ten electrode-rings, each containing four macro-electrodes, separated by four micro-electrode strips, each containing ten micro-electrodes.

A macro-electrode is a annular disc segment made of a conductive material whose radius of outer periphery equals that of the smart lead, and whose optional inner radius defines a stylus. The difference between these radii is generally greater than 0.25 mm and preferably greater than 0.50 mm. A micro-electrode also has a proximal face and an opposite distal face, both being perpendicular to the longitudinal axis. Each macro-electrode contains several through-holes parallel to the longitudinal axis that extend from the proximal face to the distal face. Each macro-electrode has an electrode-wire (made of a conductor surrounded by an insulation layer) associated with it. One end of the electrode-wire has a bared tip, made by stripping the insulation layer to a certain length. The diameter of a through-hole is slightly larger than that of the electrode-wire. A clearance is the annular empty space between a through-hole and a bared tip.

An electrical joint between a macro-electrode and an electrode-wire is formed by meshing a bared-tip of an electrode-wire with a through-hole and filling the clearance with an electrically conductive jointing medium. A nest is the set of macro-electrode joined with respective electrode-wires inside respective through-holes in this fashion. To form a smart lead body, one places the nest in a molding fixture and injects plastic material into the mold.

The micro-electrode strip comprises a micro-electrode substrate and a protection strip. The width of the micro-electrode substrate or the protection strip equals wall thickness of the macro-electrode. A first face of the micro-electrode substrate has an array of grooves that are equi-spaced and parallel to the width while an opposite face carries an array of micro-electrode traces. A first face of the protection strip also has an identical array of grooves that are equi-spaced while the opposite second face covers the array of traces. The array of grooves in the micro-electrode strip and the protection strips are used to position and lock the perforated-electrodes axially and peripherally.

One object of this invention is to provide a smart lead comprising a large number of micro-electrodes and a large number of macro-electrodes. Another object is to identify target neuron site and its boundaries with a single insertion of the lead into the brain. Another object is to reduce surgical time, reduce side-effects and increase battery life. These and other objects will be apparent after perusal of the present disclosure.

BRIEF DESCRIPTION OF THE DRAWINGS

FIG. 2 shows an electrode-ring comprising four macro-electrodes engaged to four micro-electrode strips.

FIG. 3 shows a perforated-electrode and several through-holes arranged on three pitch circles.

FIG. 4 shows an electrode-wire with a bared-tip formed by stripping insulation.

FIG. 9 shows a longitudinal section of a micro-electrode strip, comprising a micro-electrode substrate carrying an array of micro-electrode traces and engaged to a protection strip.

FIG. 10 shows a cross-section of a micro-electrode strip, comprising a micro-electrode substrate carrying an array of micro-electrode traces and engaged to a protection strip.

FIG. 11 shows a front view of a micro-electrode substrate, highlighting ten micro-electrode traces as dark lines.

FIGS. 13, 13A shows a 64-electrode smart lead that contains 64 macro-electrodes and 64 micro-electrodes.

FIGS. 14, 14A illustrates a 32-electrode smart lead that contains 32 macro-electrodes and 32 micro-electrodes.

FIGS. 15, 15A illustrates a 16-electrode smart lead that contains 16 macro-electrodes and 16 micro-electrodes.

FIGS. 16, 16A illustrates an 8-electrode smart lead that contains 8 macro-electrodes and 8 micro-electrodes.

FIG. 17 illustrates a 4-electrode smart lead that contains 4 macro-electrodes and at least 4 micro-electrodes.

FIG. 18 shows a cross-section of the 4-electrode smart lead shown in FIG. 17, highlighting a macro-electrode engaged to a micro-electrode strip.

DETAILED DESCRIPTION OF THE INVENTION

The smart lead disclosed herein contains a large number of macro-electrodes and micro-electrodes. The design, manufacture and operational principles of a smart lead are illustrated using few examples below.

Example 1

40-Electrode Smart Lead

Figure 1:
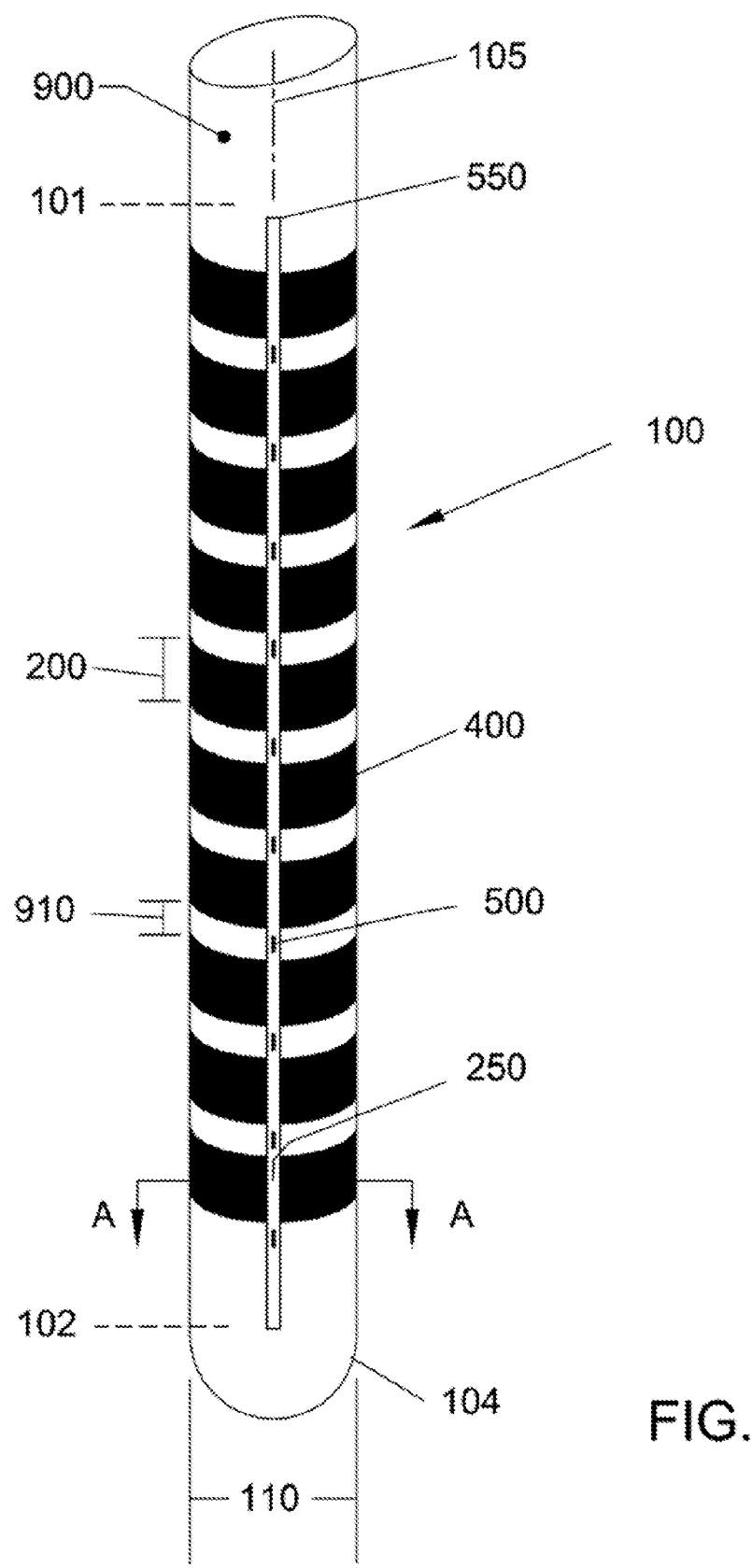
FIG. 1 shows a 40-electrode smart lead containing 40 macro-electrodes and 40 micro-electrodes between a proximal end and a distal end.

FIG. 1 shows a smart lead 100 between a proximal end 101 and a distal end 102 around a longitudinal axis 105. This elongated portion contains a stack of electrode-rings 200 separated by nine spacings 910. Each electrode-ring 200 contain four macro-electrodes 400 containing a number of through-holes separated by four radial gaps 250 each of which is filled with a micro-electrode strip 550. The number of electrode-rings preferably equals the number of through-holes. The micro-electrode strips 550 engage the macro-electrodes 400 in each of the ten electrode-rings 200 both axially and peripherally. Each micro-electrode strip 550 contains an array of ten micro-electrodes 500 and their respective traces.

FIG. 2 shows section A-A of an electrode-ring 200 that is closest to the distal end 102. The outer periphery 410 of all electrode-rings 200 contacts the nerve cells. Its inner periphery 412 contacts a stylet (not shown). The annular space between these two peripheries contains four macro-electrodes 400 separated by four radial gaps 250 which are filled with four micro-electrode strips 550. The 1st, 2nd and 3rd quadrants display a sectional view of the macro-electrodes, with the conductive solid shown hatched. The 4th quadrant displays a top view, with the conductive solid shown as a solid dark area. The macro-electrode 400 is a segment of a ring that contains ten through-holes 450 and is made of a conductive material. The bared tip 480 of electrode-wires 300, tunneled through the empty passageways formed by these through-holes 450, are electrically joined to the perforated-electrodes 400. The smart lead 100 can also be provided with lumen 120 (central blind hole) to accommodate a stylet. The lumen 120 extends up to a rounded end cap 104 at the distal end 102 of the smart lead. The end cap 104 acts as a robust stop for the stylet. A lead body 900, formed by injection molding, fills all empty spacings 910 and engages the macro-electrodes 400, micro-electrode strips 550 and the jointed electrode-wires. The lead body 900 is made of a binding material that is insulative, bio-compatible and strong, such as polyurethane, fluoropolymers etc. as known in the prior art. The lead body 900 is also called electrically insulative jointing medium, lead body material or molding material.

The smart lead 100 operates as follows. On inserts a smart lead into the brain (along a trajectory guided by non-surgical tests such as MRI). The three-dimensional array of micro-electrodes 500 sense the electrical signals from the neurons. A software embedded in an IMD uses these signals to identify the three-dimensional boundaries of the target site. The software also selects a group of macro-electrodes, identifies the stimulation parameters such as current, frequency, pulse duration etc. needed to provide best therapeutic stimulation of target neurons. The software thus automates the time-consuming tasks of target location, macro-electrode selection, parameter estimation, stimulation duration etc. Such automation reduces the time needed for actual surgery, avoids major side effects and increases battery life.

The outer diameter 110 of the smart lead 100 can range from 0.75 to 1.5 mm. Non-smart leads used by prior art had an outer diameter of 1.27 mm. A preferred smart lead 100 that is interchangeable with them will have same 1.27 mm diameter. The diameter of a lumen 120 can range from 0.20 to 0.35 mm. A preferable diameter is 0.25 mm, and optionally the smart lead 100 can be made without any lumen.

FIG. 3 shows a perforated-electrode 400 in an isometric view. This macro-electrode 400 is generally an annular disc segment made of conductive material that is perforated. The segment angle is an integral fraction of 360° (e.g., 360/2, 360/3, 360/4 etc) so that several perforated-electrodes can be fitted in an electrode-ring. A preferred perforated-electrode has an arc angle of 90°, so one can fit four perforated-electrodes 400 in an electrode-ring 200. An outer periphery 410, an opposite inner periphery 412, a proximal face 414, an opposite distal face 416, a first radial face 418 and an opposite second radial face 419 define the perforated-electrode 400. The outer periphery 410 is a segment of outer diameter of the smart lead 100. An optional inner periphery 412 is preferably a segment of the outer diameter of a lumen 120. The inner periphery can be flat, polygonal or non-existent. The proximal face 414 and distal face 416 are flat and normal to the longitudinal axis. One offsets a radial line by half the thickness of a micro-electrode strip 550 to derive the first radial face 418 and second radial face 419. The perforated-electrode 400 is made of a conductive material that is bio-compatible and non-corrosive, such as platinum-iridium alloys, MP35N etc. as known in the art.

The axial thickness "a" of a perforated-electrode 400 depends on the number of macro-electrodes and their spacing. It can be as small as 0.25 mm (for a smart lead with large number of macro-electrodes—FIG. 3). Alternatively, it can be as large as 1.5 mm (for a smart lead with few macro-electrodes—FIG. 19). A preferred smart lead 100 will have ten electrode-rings 200, each 0.5 mm thick, separated by nine 0.25 mm thick spacings 910. The electrical length of a lead, defined as axial length between outer faces of outermost electrode-rings, is 7.25 mm for the smart lead 100. This is reasonably close to the 7.5 mm electrical length of prior non-smart leads.

The radial thickness (wall) of a perforated-electrode 400 is defined as the difference between the radius of outer periphery 410 and radius of inner periphery 412. (Prior art formed macro-electrodes from thin foils that are less than 0.25 mm thick.) The radial thickness of the perforated-electrode 400 is substantially greater than 0.25 mm (0.010 inch) and generally greater than 0.5 mm (0.020 inch). For example, a preferred perforated-electrode 400 with an outer diameter of 1.27 mm and inner diameter of 0.25 mm will have a radial thickness of 0.51 mm (0.021 inch). Such larger radial thickness allows one to drill through-holes 450.

FIG. 3 shows ten through-holes 450 in the perforated-electrode 400. These through-holes 450 are empty spaces of circular section whose axes parallel to the longitudinal axis 105. They extend from the proximal face 414 to the distal face 416. These through-holes 450 are distributed along three pitch-circles as shown. The inner most pitch-circle can fit two through-holes while other pitch-circles, being larger, can fit four each. The circumferential and radial pitch of the through holes is preferably at least twice the diameter of the through-hole.

A fictitious passageway, running from the proximal end 101 to the distal end 102, is formed by aligning through-holes in different electrode rings parallel to the axis. This passageway comprises the aligned through-holes in the perforated-electrodes 400 alternating with the empty spaces in the spacings 910. The process of running an electrode-wire 300 through such fictitious passageway is called tunneling. During tunneling, the electrode-wire encounters metallic and empty spaces alternately. One through-hole in a perforated-electrode is used to join it to a tunneled electrode-wire as shown in FIG. 2. The remaining through-holes may be filled with insulative media as presented in FIGS. 5-8.

The diameter of a through-hole 450 must be slightly larger than that of an electrode-wire 300 shown in FIG. 4 to permit tunneling. The diameter of a through-hole 450 can generally range 0.025 to 0.165 mm (0.001 to 0.007 inch) depending on number of macro-electrodes. A 40-electrode smart lead can use an electrode-wire 300 of 0.05 mm (0.002 inch) diameter and a through-hole of about 0.076 mm (0.003 inch) diameter. The 0.5 mm radial thickness therefore allows one to drill ten such fine through-holes of 0.076 mm as shown in FIG. 3.

Such fine through-holes 450 can be made by several techniques, such as Micro-Electro-Discharge Machining (Micro-EDM), Laser Micro-Drilling, Electron Beam Micro-Drilling, Deep Reactive Ion Etching, Direct Micro-Drilling, etc as known in the art. For example, several manufacturers, such as Makino Tech Center, Fountain Valley, Calif. or Panasonic Factory Automation, Franklin Park, Ill. offer micro-hole EDM machines that are capable of making fine through-holes as small as 0.01 mm (0.0005 inch). The Micro-EDM is capable of producing precise micro-holes at precise locations with low out of roundness (as low as 0.001 mm), low taper, low edge burr, negligible re-cast, smaller entrance debris, smaller heat affected zone and fewer micro-cracks. The permissible aspect ratio can be as high as seventy five. The Micro-EDM method comprises the steps of manufacturing a precise plunger-electrode of required diameter and length, mounting it in a in a micro-EDM machine, precisely positioning the plunger-electrode over a macro-electrode pin using a stereo-microscope, setting control parameters such as power, voltage, advancing the plunger-electrode forward while using focused dielectric fluid to flush out the melted metal debris. Vendors such as Optimation Inc., Midvale, Utah have capabilities to produce such fine through-holes.

Alternate Laser Micro-Drilling method comprises the steps of focusing a laser over a macro-electrode, creating a starter hole and drilling through. Several manufacturers, such as Lambda Physik, Goettingen, Germany, manufacture the required precision lasers. The Electron Beam Micro-Drilling method comprises a focusing an electron beam that concentrates heat that forms a vapor capillary surrounded by molten material, which is expelled by a backing material at the underside of the macro-electrode. Manufacturers such as Coherent Inc., Santa Clara, Calif., produce such Electron Beam machines. The Deep Reactive Ion Etching uses chemical etching processes (such as photochemical machining) so requires an expensive master pattern tool.

The macro-electrodes 400 can typically be manufactured as follows. One starts with a 1.27 mm diameter, 3 mm long pins of appropriate material. Several through-holes are made in its cross-section using techniques such as Micro-EDM described above. These through-holes are then packed and sealed with a suitable particulate material (such as fine sand) to retain the strength of a through-holed pin. A 0.25 mm diameter lumen is then drilled at the center by using well-known drilling techniques. The sealed pin is then sliced using laser or EDM at 0.5 mm intervals to yield five electrode-rings. By slicing several pins at high speed at the same time, one can make forty perforated-electrodes in one-step at low cost. These perforated-electrodes are then polished by a vibratory polishing machine, which will remove any sharp edges around the through-holes.

Alternately, the perforated-electrodes can be manufactured starting with a thin sheet using the following steps. One starts with a sheet whose thickness equals the axial thickness of perforated-electrode-ring (e.g., 0.5 mm). A photographic pattern of perforated-electrodes, with through-holes built-in, is then made using photolithography. Known etching techniques such as Photo Chemical Machining are used to etch out the pattern of the perforated-electrodes on the sheet.

FIG. 4 displays an electrode-wire 300, made of a conductive core 462 (filar) shown as a thick solid line at the center, surrounded by a thin insulation layer 463. The conductor 462 carries the therapeutic current pulses while the insulation layer 463 prevents leakage of these currents to the surroundings. The conductor 462 is made of a low-resistivity material that has high strength, such as cored conductors, MP35N, platinum-indium etc as known in the art. The insulation layer 463 is made of high-durometer material with high cut-through resistance, such as polytetrafluroethylene, polyimide etc or heat-strippable insulation as known in the art. The high scratch resistance prevents damage when the electrode-wire 300 tunnels via through-holes 450.

The diameter of the electrode-wire 300 generally depends on the contact area of the macro-electrode with neurons and can range 0.05 to 0.165 mm. The contact area in a 40-electrode lead is one-tenth of that of a 4-electrode lead. Thus, a 40-electrode smart lead can employ an electrode-wire of about 0.05 mm while a 4-electrode smart lead can employ an electrode-wire of about 0.165 mm.

The electrode-wire 300 has a straight portion at one end as shown in FIG. 4. This straight portion tunnels through the fictitious passageways between the proximal end and distal end. A bared tip 480 is formed at one end of the electrode-wire by stripping the insulation layer 463 up to a length "b". This length "b" generally does not exceed the thickness "a" of the perforated-electrode 400. Preferably, "b" approximately equals "a". Such bared tip 480 can be produced by laser wire stripping (e.g., U.S. Pat. Nos. 6,265,691, 6,326,587), chemical etching, acid solvents, local burning etc as known in the art. A bared tip 480 is said to be "meshed" to a through-hole 450 when an electrode-wire 300 is tunneled longitudinally into a through-hole 450, until its annular face 482 is close to the proximal face 414 of the perforated-electrode 400 and its tip face 484 is close to the distal face 416 of the perforated-electrode 400. A bared tip 480 of an electrode-wire 300 so meshed to a through-hole 450 is used to join the electrode-wire 300 with perforated-electrode 400.

The non-straight portion of the electrode-wire 300 can be coiled, bundled, twisted, or insulated to form a stronger cable as known in the art. For example, the 40-electrode lead can use a commercially available cable of 0.012-inch diameter, comprising 10 electrode-wires, each of 0.003 inches diameter, comprising a 0.002-inch conductive core covered with an insulative layer. The non-straight portion of the electrode-wire 300 is connected to a terminal, a multiplexer, or an IMD by an extension wire as known in the art.

Figure 5:
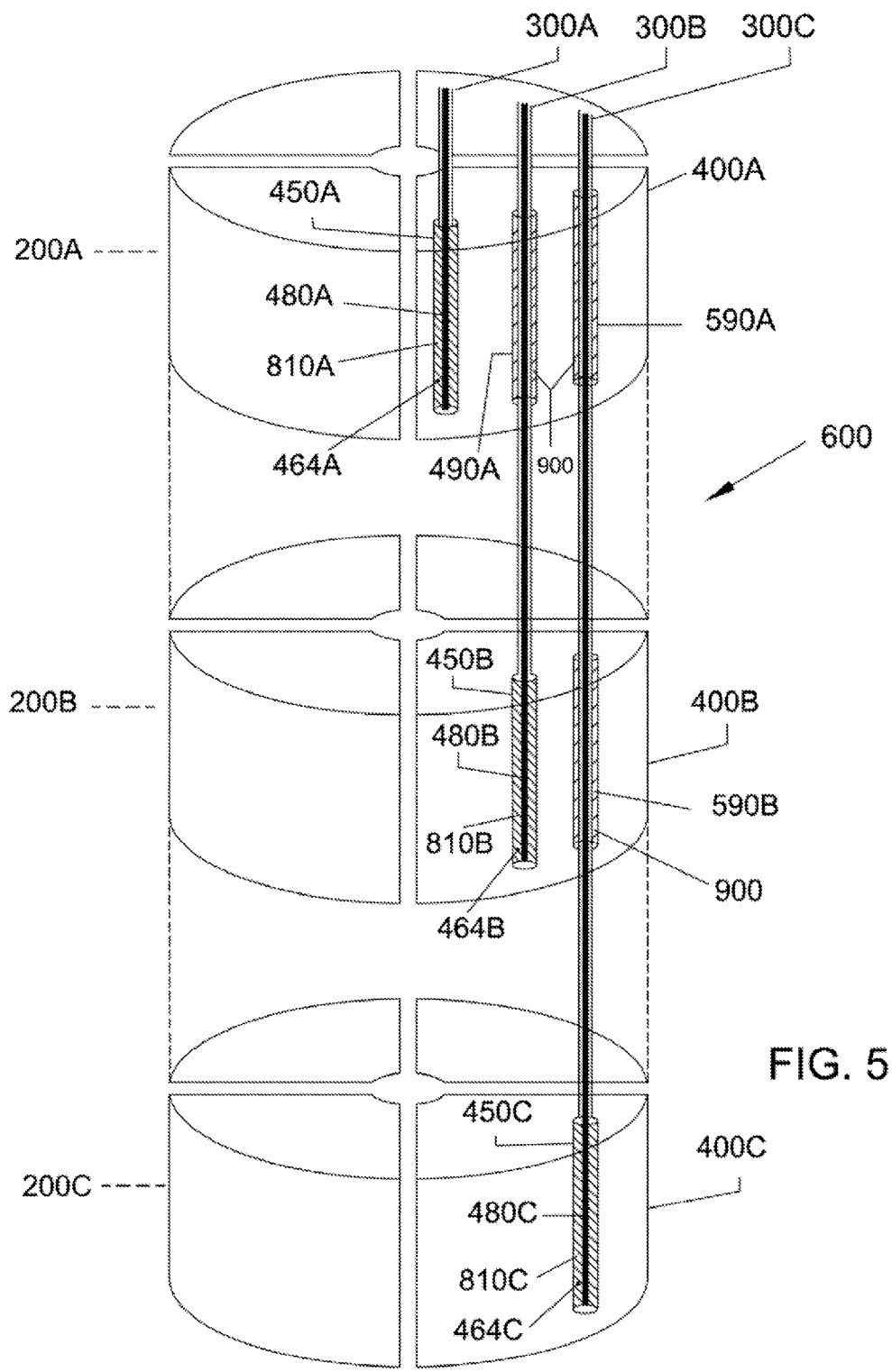
FIG. 5 shows a nest comprising a stack of electrode-rings comprising micro-electrodes joined to respective electrode-wires by electrical joints formed in respective through-holes.

FIG. 5 shows a nest 600 of the smart lead 100, comprising a stack of interconnected electrode-rings 200X with electrode-wires 300X are joined to respective perforated-electrodes 400X by electrical joints 810X that are formed in respective through-holes 450X. Here "X" can refer to any individual labels such as A, B, C . . . . The nest 600 is thus a stand-alone structure that can be handled as a separate rigid part. This figure shows three electrical joints 810X in three electrode-rings 200X. For clarity, it does not show the four micro-electrode strips that engage the macro-electrodes. These electrical joints are formed inside the through-holes 450X in an orderly fashion as described below.

A first electrical joint 810A (between a first bared tip 480A of a first electrode-wire 300A and a first macro-electrode 400A) is formed inside a first through-hole 450A of the first macro-electrode 400A as follows. The first bared tip 480A is meshed with this through-hole 450A. The clearance between the two is filled with an electrically conductive jointing medium 464 to form the first electrical joint 810A. Electric current can then flow from the first electrode-wire 300A via the first electrical joint 810A into the first macro-electrode 400A.

A second electrical joint 810B (between a second bared tip 480B of a second electrode-wire 300B and a second macro-electrode 400B) is formed inside a second through-hole 450B of the second macro-electrode 400B as follows. The second bared tip 480B is meshed with this through-hole 450B. The clearance between the two is filled with an electrically conductive jointing medium 464A to form the second electrical joint 810B. The second electrode-wire 300B is tunneled via an intermediate through-hole 490A in the first macro-electrode 400A in its path. The wire and hole are electrically isolated by filling a clearance between the two with electrically insulative jointing medium 900. Electric current can then flow from the second electrode-wire 300B via the second electrical joint 810B into the second macro-electrode 400B.

A third electrical joint 810C (between a third bared tip 480C of a third electrode-wire 300C and a third macro-electrode 400C) is formed inside a third through-hole 450C of the third micro-electrode 400C as follows. The third bared tip 480C is meshed with this through-hole 450C. The clearance between the two is filled with an electrically conductive jointing medium 464C to form the third electrical joint 810C. The third electrode-wire 300C is tunneled via an intermediate through-hole 590A in the first macro-electrode 400A and an intermediate through-hole 590B in the second macro-electrode 400B that are in its path. The electrode-wire 300C is electrically isolated from 590A and 590B by filling a clearance between the two with an electrically insulative jointing medium. This jointing medium is preferably identical to the lead body material 900. Electric current can then flow from the third electrode-wire 300C via the third electrical joint 810C into the third macro-electrode 400C. A person skilled in the art can construe formation of remaining electrical joints in a similar fashion.

Figure 6:
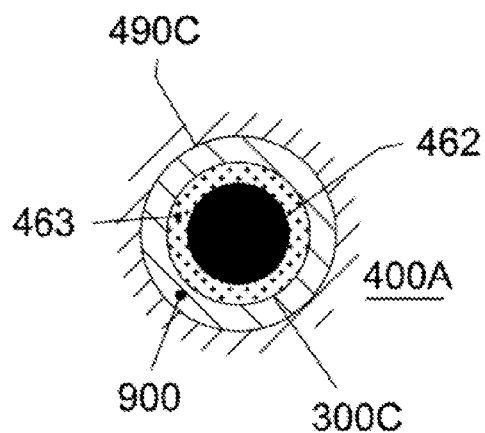
FIG. 6 illustrates how an electrode-wire is electrically isolated from an intermediate through-hole through which it tunnels.

FIG. 6 illustrates how the third electrode-wire 300C is electrically isolated from intermediate through-holes 490C while tunneling. The third electrode-wire 300C is made of a conductor 462 covered by an insulative layer 463. An electrically insulative jointing material 900 fills the clearance between the third electrode-wire 300C and intermediate through-hole 490C. So, both the insulative layer 463 and the electrically insulative jointing material 900 prevent passage of current from the conductor 462 into the intermediate through-hole 490C. The clearance between the third electrode-wire 300C and intermediate through-hole 490C can be more than 0.0125 mm (0.0005 inch). Such clearance is known in the ANSI B4.1 specification as a sliding fit RC1. This fit is sufficient to slide the third electrode-wire 300C through the intermediate through-hole 490C without damaging the insulation layer 463. Optionally, a looser fit, known as the running fit RC2, could also be employed to further protect the insulation layer 463.

Figure 7:
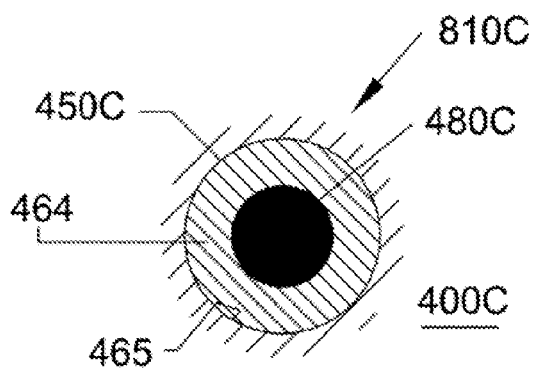
FIG. 7 shows a cross-section of an electrical joint (between an electrode-wire and a macro-electrode) inside a through-hole.

FIG. 7 shows a cross-section of the third electrical joint 810C (between the third electrode-wire 300C and a third macro-electrode 400C) inside the third through-hole 450C. This joint is made of an electrically conductive jointing medium 464 between the third bared tip 480C and the through-hole 450C. Electrical current passes from the bared tip 480C via the electrically conductive jointing medium 464 into the third through-hole 450C and hence into the third macro-electrode 400C.

Figure 8:
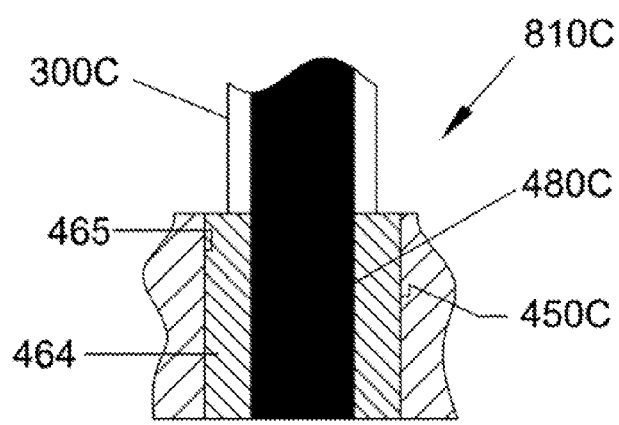
FIG. 8 shows a longitudinal section of an electrical joint inside a through-hole.

FIG. 8 shows a longitudinal section of the third electrical joint 810C inside the through-hole 450C. An electrically conductive jointing medium 464 filled the annular space bounded by the bared tip 480C and the inner periphery 465 of the third through-hole 450C. In the preferred embodiment shown, the third bared tip 480C is meshed with the third through-hole 450C. The length of the third electrical joint 810C equals that of the macro-electrode (0.5 mm). This is 400% larger the 0.125 mm used in the prior art. As a result, this electrical joint 810C is significantly stronger.

The term "electrical joint" herein refers to any means such as welding, soldering, conductive adhesive bonding etc, by which two conductive solids are joined together, so that electric current flows from one part to the other part. Different conductive jointing media (such as conductive epoxy, molten solder, solder paste etc.) with different processes (such as laser, resistance, ultrasonic or spot welding, high-voltage etc) can be used to create an electrical joint as known in the art. For example, a joint using an electrically conductive epoxy can be made by filling a through-hole with the epoxy, dipping the bared tip into the epoxy-filled hole, wiping out the overflow epoxy from the faces of the macro-electrode, and curing the conductive epoxy. Several low-viscosity bio-compatible epoxies, e.g., Epotek H20E from Epoxy Technology, Inc., Billercia, Mass. can be used to form such electrical joint. Alternately, one can use solder paste. Alternatively, the joint can be made by inserting a tinned bared tip that protrudes out of the electrode slightly and heating the tinned tip with a soldering iron to remelt the solder.

Figure 12:
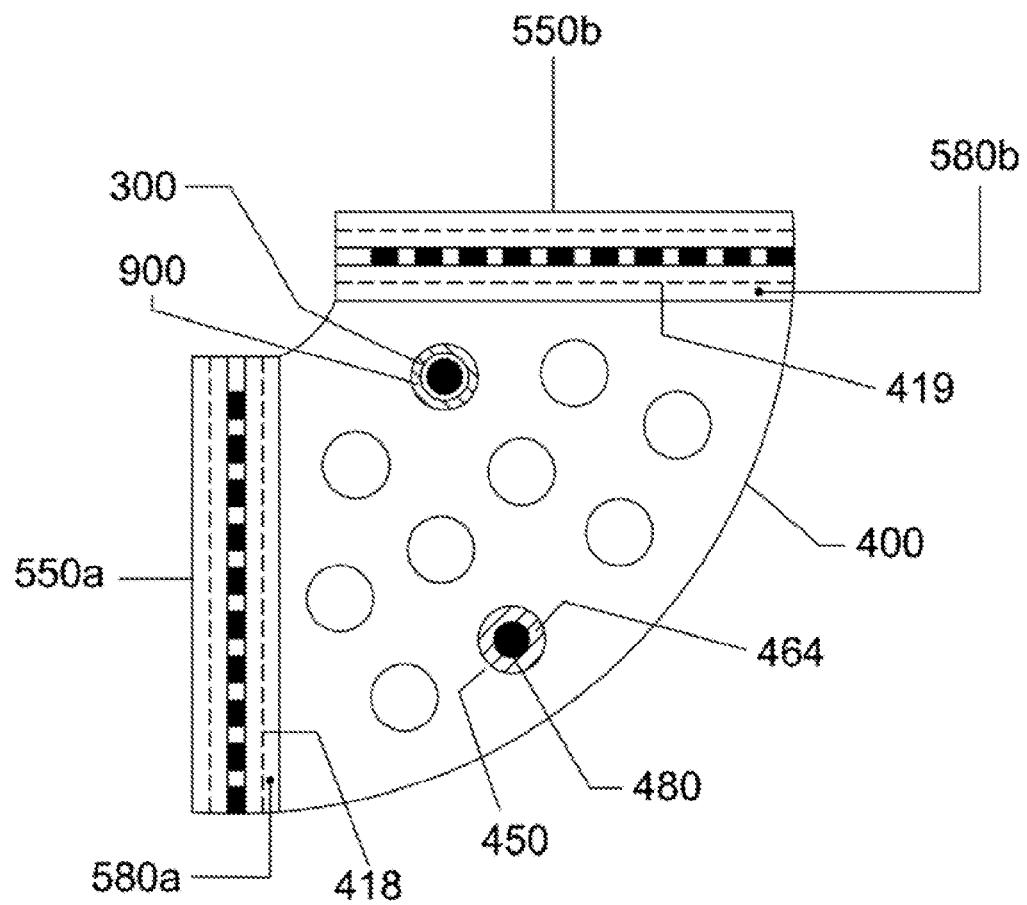
FIG. 12 shows a macro-electrode locked between two micro-electrode strips and immobilized by an electrical joint with an electrode-wire in a through-hole.

FIG. 9 shows a micro-electrode strip 550 in longitudinal section, comprising a micro-electrode substrate 552 carrying an array of micro-electrode traces 554 and engaging a protection strip 556. These micro-electrode traces 554 are sandwiched between the micro-electrode substrate 552 and the protection strip 556. The micro-electrode substrate 552 is an elongated rectangular strip, made of a bio-compatible insulative material that discourages attachment of neurons such as silicon nitride. The width of both micro-electrode substrate 552 and protection strip 556 equals the radial thickness of a perforated-electrode 400. Its length generally exceeds the electrical length of the smart lead. A first face of the micro-electrode substrate 552 and a first face of the protection strip 556 have an array of grooves 580 (ten in a preferred smart lead 100). This array of grooves are equi-spaced and laid parallel to the width of the micro-electrode substrate. These grooves are used to position and assemble the macro-electrodes 400 as shown in FIG. 12. A preferred micro-electrode substrate 552 is 0.5 mm wide and 8 to 10 mm long. The groove length 582 equals the axial thickness "a" of a perforated-electrode 400. The groove depth 584 can range 0.025 to 0.10 mm (0.001 to 0.004 inch). These grooves 580 can be made using known techniques such as machining, laser, etching etc.

FIG. 10 shows a micro-electrode strip 550 but in cross-section, viz. a zoomed view of that in FIG. 2. The micro-electrode strip 550 comprises an elongated micro-electrode substrate 552 carrying an array of micro-electrode traces 554 and engaged to a protection strip 556. The sum of thickness of the micro-electrode substrate 552, micro-electrode traces 554 and the protection strip 556 equals the radial gap between successive perforated-electrodes 400.

FIG. 11 shows a front view of the micro-electrode substrate, highlighting the ten micro-electrode traces 554. The micro-electrode traces 554 have rectangular cross section and are electro-deposited or etched on a second face of the micro-electrode substrate 552 using conventional printed circuit board (PCB) techniques. The traces are made of a bio-compatible conductive material such as gold, silver, iridium, platinum, titanium etc, as known in the art. The micro-electrode trace 554 is L-shaped, with a short leg 560 (that runs parallel to width of the micro-electrode strip 550) and a long leg 570 (that run parallel to length of the micro-electrode strip 550), both equi-spaced at different pitches. The length of short leg 560 and the long leg 570 increases from the proximal end 101 to the distal end 102. The long leg 570 terminates at the proximal end 101 where the micro-electrode traces are connected to electrode-wires, a multiplexer or a contact pad (not shown) which are in turn connected to a IMD as known in the art. Both legs meet at the bend 590, which is chamfered to reduce concentration of currents.

A micro-electrode 500 refers to the edge face of the short leg 560 of a micro-electrode trace 554. When assembled, this micro-electrode 500 is flush with the outer periphery of the lead, so it is in contact with the neurons. The sectional area of a micro-electrode is generally one to three orders of magnitude smaller than that of a macro-electrode. Such small area allows the micro-electrode 500 to sense the firing patterns of one or more neurons. The axial pitch of the micro-electrode is chosen to accommodate the required number of micro-electrodes 500 within the electrical length. These micro-electrodes 500 can generally be positioned at arbitrarily location along the electrical length. In a preferred embodiment, they are located in the mid-plane of the electrode-rings or mid-plane of spacer rings. The air gap space between successive micro-electrode traces can range 0.010 to 0.25 mm. The width and height of each micro-electrode trace can generally range 0.005 to 0.1 mm. A preferable micro-electrode trace 554 has width of about 0.030 mm and height of about 0.025 mm. This is comparable to a prior-art micro-electrode, which is an insulated conductor of 0.005 to 0.050 mm diameter.

FIG. 12 shows a macro-electrode 400 engaged to a first micro-electrode strip 550a and a second micro-electrode strip 550b. The first radial face 418 of the macro-electrode 400 fits inside a first groove 580a of the first micro-electrode strip 550a. The second radial face 419 of the macro-electrode 400 fits inside a second groove 580b of the second micro-electrode strip 550b. The first micro-electrode strip 550a and the second micro-electrode strip 550b thus prevent the movement of the macro-electrode 400 both in the longitudinal direction and in the peripheral direction. The macro-electrode 400 is also locked by an array of joints between electrode-wires and through-holes. For example, a bared tip 480 is jointed in a through-hole 450 of the macro-electrode 400 is jointed with an electrically conductive jointing medium 464. Other electrode-wires 300 tunneling via intermediate through-holes are jointed with electrically insulative jointing medium 900. All these joints prevent movement of the electrode in axial and radial direction. The macro-electrode 400 is thus locked in all directions by two micro-electrode strips and an array of joints. As a result, a macro-electrode 400 cannot be dislodged out of the lead, so it cannot get entangled in the brain.

The smart lead 100 can be manufactured using several techniques such as injection molding, vacuum impregnation, vacuum-assisted resin transfer molding (VARTM), epoxy molding etc as known in the art. A preferred method uses insert injection molding as follows. A mold with a cavity that is a negative image of the smart lead 100 and its end-cap (with an entry hole for the molding plastic material at the tip of the end-cap and an exit hole at the proximal end) is constructed. A central rod that mirrors the lumen is affixed at the proximal end. The nest 600 comprising electrodes, wires and micro-electrode strips, that was fabricated beforehand is hung around this round rod. The molding material 900 is then injected at a high pressure and high temperature. The injected material binds all the parts, viz., the electrode-wires, macro-electrodes, micro-electrodes, electrical joints, spacings, end cap etc. It fills the large spacings between the macro-electrodes. It also fills the small clearances between the through-holes and electrode-wires thereby bonding the electrode-wires to the macro-electrodes. It also flows into all empty through-holes within the macro-electrodes, further binding the lead with the nest. It also fills the hollow space at the distal end, thereby forming the end-cap. This results in a strong lead with all macro-electrodes, micro-electrodes and electrode-wires inseparable from the lead. Therefore, the electrodes cannot be entangled in the brain.

Example 2

64-Electrode Smart Lead

FIGS. 13, 13A show a 64-electrode smart lead 1002 that contains 64 macro-electrodes 4002 and 64 micro-electrodes 5002. All these electrodes are contained in 16 electrode-rings 2002, each carrying 4 macro-electrodes 4002, bound by 4 micro-electrode strips 5502, each carrying 16 micro-electrodes. These electrode-rings 2002 are equi-spaced axially between the proximal end and the distal end of the smart lead 1002. Each electrode-ring 2002 comprises four perforated-electrodes 4002 in four quadrants. The zoomed sectional view in FIG. 13A shows how each perforated-electrode 4002 contains 16 through-holes 4502 in three pitch circles. These through-holes 4502 are used to join individual perforated-electrodes 4002 with associated bared tips 4802 in a manner similar to that described in earlier paragraphs. The four perforated-electrodes 4002 are held together by four micro-electrode strips 5502, which run longitudinally as radial spokes. Each micro-electrode strip 5502 carries sixteen micro-electrodes 5002 plus their micro-electrode traces on an insulative micro-electrode substrate and covered by a protection strip. A person skilled in the art can easily deduce the constructional features of the 64-electrode smart lead 1002 from that of the 40-electrode smart lead 100 that is described earlier. A subset of such 64-electrodes can then be used to focus the currents to inside a target site, thereby reducing side effects. Because of high resolution, the 64-electrode smart lead 1002 can thus reduce surgical time, harmful side-effects and increase battery life.

Example 3

32-Electrode Smart Lead

FIGS. 14, 14A show a 32-electrode smart lead that 1003 contains 32 macro-electrodes 4003 and 32 micro-electrodes 5003. All these electrodes are contained in 8 electrode-rings 2003, each carrying 4 macro-electrodes 4002, bound by 4 micro-electrode strips 5502, each carrying 8 micro-electrodes. These electrode-rings 2003 are equi-spaced axially between the proximal end and the distal end of the smart lead 1003. Each electrode-ring 2003 comprises four perforated-electrodes 4003 in four quadrants. The zoomed sectional view in FIG. 14A shows how each perforated-electrode 4003 contains 8 through-holes 4503 in two pitch circles. Alternately, these through-holes can be distributed in three pitch circles. These through-holes 4503 are used to join individual perforated-electrodes 4003 with associated bared tips 4803 in a manner similar to that described in earlier paragraphs. The four perforated-electrodes 4003 are held together by four micro-electrode strips 5503, which run longitudinally as radial spokes. Each micro-electrode strip 5503 carries eight micro-electrodes 5003 plus respective micro-electrode traces on an insulative substrate and covered by a protection strip. A person skilled in the art can easily deduce the constructional features of the 32-electrode smart lead 1003 from that of the 40-electrode smart lead 100 that is described earlier. A subset of such 32-electrodes can then be used to focus the currents to inside a target site, thereby reducing side effects. Because of high resolution, the 32-electrode smart lead 1003 can reduce surgical time, harmful side-effects and increase battery life.

Example 4

16-Electrode Smart Lead

FIGS. 15, 15A show a 16-electrode smart lead 1004 that contains 16 macro-electrodes 4004 and 16 micro-electrodes 5004. All these electrodes are contained in 4 electrode-rings 2004, each carrying 4 macro-electrodes 4002, bound by 4 micro-electrode strips 5502, each carrying 4 micro-electrodes. These electrode-rings 2004 are equispaced axially between the proximal end and the distal end of the smart lead 1004. Each electrode-ring 2004 comprises four perforated-electrodes 4004 in four quadrants. The zoomed sectional view in FIG. 15A shows how each perforated-electrode 4004 contains 8 through-holes 4503 in two pitch circles. These through-holes 4504 are used to join individual perforated-electrodes 4004 with associated bared tips 4804 in a manner similar to that described in earlier paragraphs. The four perforated-electrodes 4004 are held together by four micro-electrode strips 5504, which run longitudinally as radial spokes. Each micro-electrode strip 5504 carries four micro-electrodes 5004 plus respective micro-electrode traces on an insulative substrate and covered by a protection strip. A person skilled in the art can easily deduce the constructional features of the 16-electrode smart lead 1004 from that of the 40-electrode smart lead 100 that is described earlier. A subset of such 16-electrodes can then be used to focus the currents to inside a target site, thereby reducing side effects. Because of high resolution, the 16-electrode smart lead 1003 can reduce surgical time, harmful side-effects and increase battery life.

Example 5

8-Electrode Smart Lead

FIGS. 16, 16A show an 8-electrode smart lead 1005 that contains 8 macro-electrodes 4005 and 8 micro-electrodes 5005. All these electrodes are contained in 4 electrode-rings 2005, each carrying 2 macro-electrodes 4005, bound by 2 micro-electrode strips 5505, each carrying 4 micro-electrodes. These electrode-rings 2005 are equispaced axially between the proximal end and the distal end of the smart lead 1005. Each electrode-ring 2005 comprises two perforated-electrodes 4005 in two semi-circles. The zoomed sectional view in FIG. 16A shows how each perforated-electrode 4005 contains 4 through-holes 4505 in a pitch circle. These through-holes 4505 are used to join individual perforated-electrodes 4005 with associated bared tips 4805 in a manner similar to that described in earlier paragraphs. The two perforated-electrodes 4005 are held together by two micro-electrode strips 5505, which run longitudinally as radial spokes. Each micro-electrode strip 5505 carries four micro-electrodes 5005 plus respective micro-electrode traces on an insulative substrate and covered by a protection strip. A person skilled in the art can easily deduce the constructional features of the 8-electrode smart lead 1005 from that of the 40-electrode smart lead 100 that is described earlier.

Example 6

4-Electrode Smart Lead

FIG. 17 shows a 4-electrode smart lead 1006 that contains four macro-electrodes 4006 and at least four micro-electrodes 5006. The four macro-electrodes 4006 are stacked axially between a proximal end 1016 to distal end 1026, separated by three empty spacings 9106. All macro-electrodes 4006 have four through-holes, one of which is used to join it with an associated bared tip 4806 (FIG. 18). Each has a radial slit 2506 that is aligned along the longitudinal axis. A micro-electrode strip 5506 fitted in this radial slit 2506 locks all macro-electrodes. The smart lead 1006 can be provided with lumen 1206 (central blind hole) to accommodate a stylet that is used to guide it inside the brain. The lumen 1206 extends up to a rounded end cap 1046 at the distal end 1026. The end cap 1046 acts as a robust stop for the stylet. The diameter of the lumen is preferably identical to that of commercially available stylets. A lead body 9006 is made of injection moldable binding material that is insulative, strong and bio-compatible as known in the prior art. The injection molding fills all empty spacings 9106 and engages all macro-electrodes. It also fills all other empty spaces to engage the macro-electrodes 4006, electrode-wires 3006 and micro-electrode strips 5506.

The smart lead 1006 operates as follows. It is inserted into the brain (along a pre-determined trajectory determined from non-surgical tests such as MRI, CT). The electrical signals from the neurons are sensed by the array of micro-electrodes 5006. A software embedded in an IMD uses these signals to locate the boundaries of target neuron site. The software also selects specific macro-electrodes and identifies the stimulation parameters such as current, frequency, pulse duration etc. needed to provide best therapeutic stimulation of target neurons. The software thus performs closed loop control of the time-consuming tasks of target location, macro-electrode selection, parameter estimation, neuron stimulation etc. Such automation reduces the time needed for actual surgery. It also applies focused currents to the target neurons only, so avoids major side-effects.

A preferred smart lead 1006 that is interchangeable with a commercial leads will have same diameter of 1.27 mm. The axial thickness of a macro-electrode, synchronized with that of a prior art non-smart DBS lead, is 1.5 mm. The axial thickness of the spacing, can be either 0.5 mm or 1.5 mm, and is synchronized with that of prior-art non-smart leads.

FIG. 18 shows a zoomed sectional view along the line AA of a macro-electrode 4006 that is closest to the distal end 1026. The macro-electrode 4006 is a conductive annulus with a radial slit 2506. This radial slit 2506 is filled with a micro-electrode strip 5506 which locks the macro-electrodes 4006. Four through-holes 4506 spaced 90° apart are provided in the macro-electrode 4006 as shown. Its pitch circle 4516 is preferably the mean diameter of the macro-electrode 4006. All through-holes in different macro-electrodes are aligned in the axial direction, and form a fictitious passageway that runs from proximal end 1016 to distal end 1026. The diameter of the through-holes 4506 is slightly larger than that of an electrode-wire 3006. This creates a small clearance 4756 between an electrode-wire 3006 and a through-hole 4506. This small clearance 4756 allows an electrode-wire 3006 to tunnel via the fictitious passageway. One of the through-hole is used to join a macro-electrode to a bared tip 4806 of an electrode-wire using an electrically conductive jointing medium 4646 as described earlier.

The micro-electrode strip 5506 comprises a substrate carrying at least four micro-electrodes 5006 and respective traces covered by a protection strip in a fashion similar to that shown in FIG. 9-11. Optionally more than 4 micro-electrodes 5006 can be provided to increase the accuracy. The thickness of the micro-electrode strip substantially equals that of the radial slit 2506. The micro-electrode strip 5506 is engaged into the radial slit 2506 by techniques such as epoxy bonding, soldering etc as known in the art.

Figure 19:
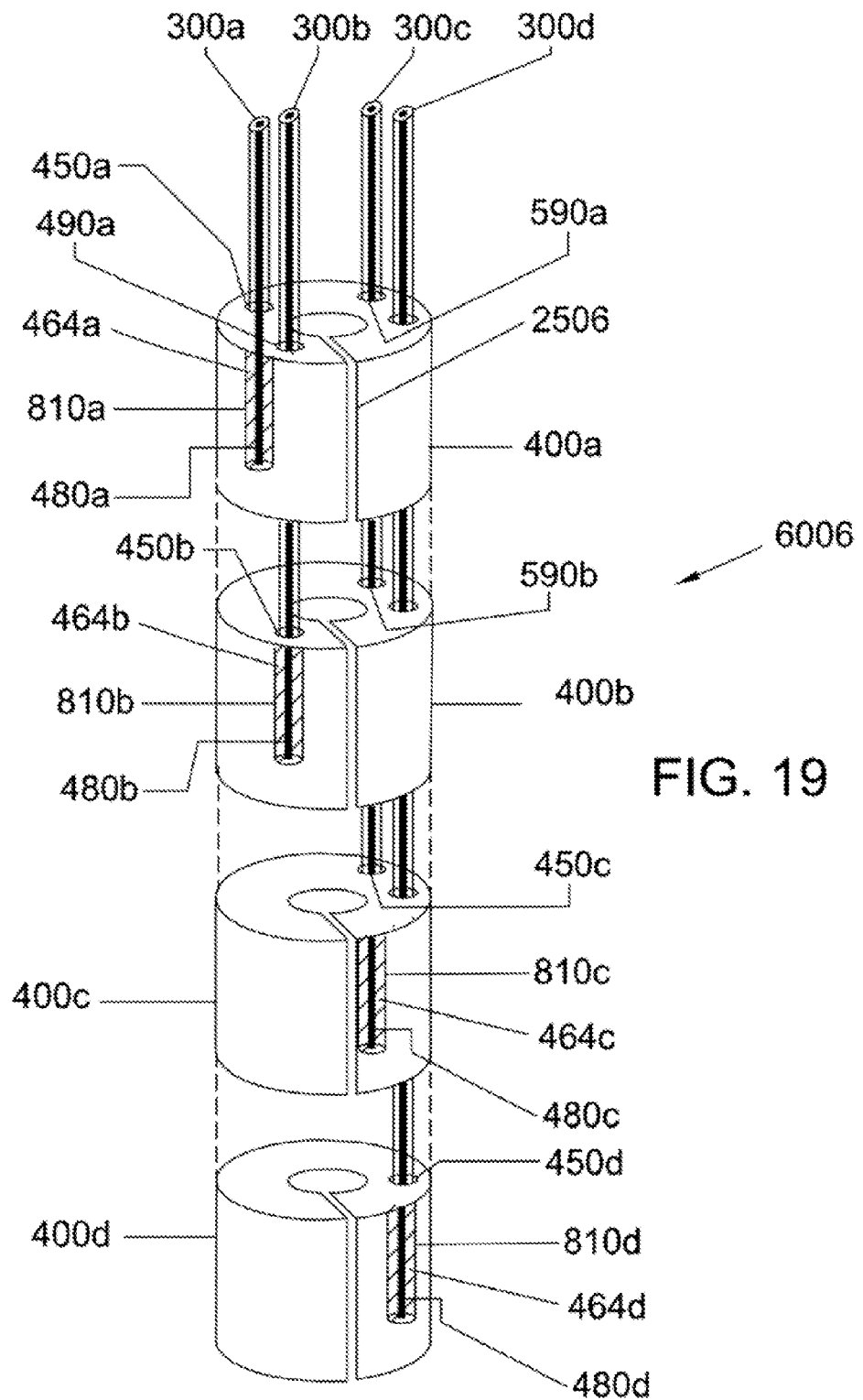
FIG. 19 is a cutout view of the 4-electrode smart lead, showing electrical joints between the 4 macro-electrodes and respective electrode-wires.

FIG. 19 is a nest 6006 of the smart lead 1006, comprising a stack of macro-electrodes 400x joined with respective electrode-wires 300x by electrical joints 810x that are formed in respective through-holes 450x. Here "x" can refer to any individual labels such as a, b, c, . . . . The nest 6006 is thus a stand-alone structure that can be handled as a separate rigid part. For clarity, it does not show the micro-electrode strip that engage the macro-electrodes in its radial slits 2506. These electrical joints are formed inside the through-holes 450x in an orderly fashion as described below.

A first electrical joint 810a (between a first bared tip 480a of a first electrode-wire 300a and a first macro-electrode 400a) is formed inside a first through-hole 450a of the first macro-electrode 400a as follows. The first bared tip 480a is meshed with this through-hole 450a. The clearance between the two is filled with an electrically conductive jointing medium 464a to form the first electrical joint 810a. Electric current can then flow from the first electrode-wire 300a via the first electrical joint 810a into the first macro-electrode 400a.

A second electrical joint 810b (between a second bared tip 480b of a second electrode-wire 300b and a second macro-electrode 400b) is formed inside a second through-hole 450b of the second macro-electrode 400b as follows. The second bared tip 480b is meshed with this through-hole 450b. The clearance between the two is filled with an electrically conductive jointing medium 464b to form the second electrical joint 810b. The second electrode-wire 300b is tunneled via an intermediate through-hole 490a in the first macro-electrode 400a in its path. The wire and hole are electrically isolated by filling a clearance between the two with electrically insulative jointing medium. Electric current can then flow from the second electrode-wire 300b via the second electrical joint 810b into the second macro-electrode 400b.

A third electrical joint 810c (between a third bared tip 480c of a third electrode-wire 300c and a third macro-electrode 400c) is formed inside a third through-hole 450c of the third micro-electrode 400c as follows. The third bared tip 480c is meshed with this through-hole 450c. The clearance between the two is filled with an electrically conductive jointing medium 464c to form the third electrical joint 810c. The third electrode-wire 300c is tunneled via an intermediate through-hole 590a in the first macro-electrode 400a and an intermediate through-hole 590b in the second macro-electrode 400b that are in its path. The electrode-wire 300c is electrically isolated from 590a and 590b by filling a clearance between the two with an electrically insulative jointing medium 900. Electric current can then flow from the third electrode-wire 300c via the third electrical joint 810c into the third macro-electrode 400c. A fourth electrical joint 810d (between a fourth bared tip 480d of a fourth electrode-wire 300d and a fourth macro-electrode 400d) is formed inside a third through-hole 450d of the fourth micro-electrode 400d in similar fashion as described in paras [0053] to [0055].

The principles disclosed herein can be used to construct leads with other arbitrary number of macro-electrodes. A person skilled in the art can easily make minor modifications, such as number electrode-rings, macro-electrodes, micro-electrodes etc. without altering the scope of the present disclosure. Now that the smart lead is described, its significant advancement in the state of the art can be fully appreciated, some of which are described below.

The smart lead can be used in virtually any neuromodular lead market. These markets include: Deep Brain Stimulation (DBS) for Parkinson's disease, Spinal Cord Stimulation (SCS) for chronic pain, Vagal Nerve Stimulation (VNS) for epilepsy, Peripheral Nerve Stimulation (PNS) for incontinence, cardio leads, defibrillators, etc.

The smart lead can significantly reduce harmful side effects. It restricts the currents to target neurons and does not stimulate non-target neurons, so reduces the side effects. The smart lead can greatly reduce the time needed for surgery. The micro-electrodes built into the smart lead allows one to automate the time-consuming tasks of optimal positioning of the lead, selection of macro-electrodes, estimating strength of stimulation currents etc, thereby saving surgical time. The smart lead can greatly increase the battery life. By minimizing the macro-electrodes needed, it can greatly reduce the energy needed to stimulate the target neurons and hence increase the battery life.

The electrodes in the smart lead can never get entangled in the brain. The macro-electrodes are firmly jointed to the electrode-wires and micro-electrode strips; they are also bonded to the lead body, so they cannot be entangled in the brain. The micro-electrodes are sandwiched between strips, so they cannot get entangled in the brain. The electrical joints in the smart lead can never cause damage the brain tissue. The joints between the electrode-wire and macro-electrodes are buried in the through-holes inside the macro-electrode, and does not come in contact with brain tissue. Therefore, the joints cannot cause damage to the brain. The joints in the smart lead can rarely fail. They are hidden deeply inside the through-holes, so are protected from mechanical abuse. The electrode-wires in the smart lead rarely fail by fatigue. These electrode-wires are bonded to the macro-electrodes and the lead body. They are not subjected to handling stresses and do not fail by fatigue.

The smart lead simplifies manufacturing process. It eliminates the steps of laser machining several grooves on the lead body to engage macro-electrodes. It eliminates a separate substrate for supporting the macro-electrode. It eliminates drilling holes in the substrate and macro-electrode for welding the electrode-wire to macro-electrode. It eliminates precise bending a tip of electrode-wires and looping it through a hole in the substrate and a hole in the macro-electrode. The smart lead is economical to manufacture. It can be mass-produced at low cost by insert molding. It requires fewer steps for manufacture, which greatly reduces the assembly and labor costs.

A smart lead is inserted into target site and its micro-electrodes and macro-electrodes are electrically connected to an IMD. The IMD contains a feedback controller that uses sensed signals to define the boundaries of a target volume. The controller also selects the macro-electrodes and strength of therapeutic currents to be applied. Once the lead is implanted within the brain, the feedback controller automates the processes of locating the target and its boundaries, defining the macro-electrodes and the therapeutic current pattern to be applied. The controller selects macro-electrodes that only stimulate those brain cells inside the target site thereby avoiding side effects. The controller will also determine when and how stimulation should occur, so will increase battery life. Once installed, the controller can be tuned to look for patient's abnormal neural firing patterns that indicate some ailments. It is then programmed to automatically apply regulated currents to disrupt the abnormal activity and bring back stable conditions. Conventional stimulators stimulate 24 hrs a day, while a smart lead with smart controller allows stimulation only when required, say 5 minutes a day, so significantly increases battery life.

I claim:

1. An implantable lead having a longitudinal axis, comprising:
   (a) a plurality of macro-electrodes, each macro-electrode shaped as annular disc segment spanning an integral fraction of 360°, said each macro-electrode having a plurality of electrodes separated by a plurality of radial gaps, wherein said plurality of electrodes form an electrode-ring,
   b) a plurality of micro-electrode strips, each micro-electrode strip comprising an insulative micro-electrode substrate with an array of micro-electrode traces, and a protection strip, wherein said protection strip covers said array of micro-electrode traces,
   wherein said plurality of macro-electrodes are engaged and locked together by said plurality of micro-electrode strips which are placed in said radial gaps of said each macro-electrode and wherein said plurality of micro-electrode strips extend in a direction parallel to the longitudinal axis.

2. The implantable lead in claim 1, wherein the implantable lead is formed with a molding material that is insulative and bio-compatible that fills all empty spaces and engages said macro-electrodes and said micro-electrode strips.

* * * * *